US009968531B2

(12) United States Patent
Albert et al.

(10) Patent No.: US 9,968,531 B2
(45) Date of Patent: May 15, 2018

(54) DEODORANTS CONTAINING 1,3-PROPANEDIOL

(71) Applicant: DuPont Tate & Lyle Bio Products Company, LLC, Loudon, TN (US)

(72) Inventors: Rose D. Albert, Richboro, PA (US); John M. Chandler, Bear, DE (US); Stephen J. Hurff, Newark, DE (US)

(73) Assignee: DUPONT TATE & LYLE BIO PRODUCTS COMPANY, LLC, Loudon, TN (US)

( * ) Notice: Subject to any disclaimer, the term of this patent is extended or adjusted under 35 U.S.C. 154(b) by 0 days. days.

(21) Appl. No.: 15/229,850

(22) Filed: Aug. 5, 2016

(65) Prior Publication Data

US 2017/0035666 A1 Feb. 9, 2017

Related U.S. Application Data

(60) Provisional application No. 62/201,261, filed on Aug. 5, 2015.

(51) Int. Cl.
*A61K 8/34* (2006.01)
*A61Q 15/00* (2006.01)
*A61K 8/86* (2006.01)

(52) U.S. Cl.
CPC ............. *A61K 8/345* (2013.01); *A61K 8/86* (2013.01); *A61Q 15/00* (2013.01); *A61K 2800/262* (2013.01); *A61K 2800/30* (2013.01); *A61K 2800/874* (2013.01)

(58) Field of Classification Search
None
See application file for complete search history.

(56) References Cited

U.S. PATENT DOCUMENTS

| | | | |
|---|---|---|---|
| 4,486,334 A | 12/1984 | Horiuchi et al. | |
| 4,617,185 A | 10/1986 | DiPietro | |
| 4,816,261 A | 3/1989 | Luebbe et al. | |
| 4,897,220 A | 1/1990 | Trieselt et al. | |
| 4,906,454 A * | 3/1990 | Melanson, Jr. | A61K 8/4926 424/401 |
| 5,531,927 A | 7/1996 | Peters | |
| 5,576,340 A | 11/1996 | Fujita et al. | |
| 5,633,362 A | 5/1997 | Nagarajan et al. | |
| 5,686,276 A | 11/1997 | Laffend et al. | |
| 5,716,604 A | 2/1998 | Coe et al. | |
| 5,821,092 A | 10/1998 | Nagarajan et al. | |
| 6,025,184 A | 2/2000 | Laffend et al. | |
| 6,123,932 A | 9/2000 | Guskey et al. | |
| 6,136,576 A | 10/2000 | Diaz-Torres et al. | |
| 6,174,521 B1 | 1/2001 | Li et al. | |
| 6,348,200 B1 | 2/2002 | Nakajima et al. | |
| 6,358,499 B2 | 3/2002 | Hall-Puzio et al. | |
| 6,358,716 B1 | 3/2002 | Bulthuis et al. | |
| 6,361,983 B1 | 3/2002 | Ames | |
| 6,406,895 B1 | 6/2002 | Defretin et al. | |
| 6,428,767 B1 | 8/2002 | Burch et al. | |
| 6,479,716 B2 | 11/2002 | Hlialy et al. | |
| 6,555,700 B1 | 4/2003 | Horrobin et al. | |
| 6,726,887 B1 | 4/2004 | Sugarman | |
| 7,063,834 B2 | 6/2006 | Mougin et al. | |
| 7,098,368 B2 | 8/2006 | Seapan et al. | |
| 7,759,393 B2 | 7/2010 | Joerger et al. | |
| 8,048,920 B2 | 11/2011 | Joerger et al. | |
| 8,309,116 B2 | 11/2012 | Fenyvesi et al. | |
| 2002/0035161 A1 | 3/2002 | Segura et al. | |
| 2002/0048557 A1* | 4/2002 | Cai | A61K 8/042 424/65 |
| 2002/0098217 A1 | 7/2002 | Piot et al. | |
| 2003/0082756 A1 | 5/2003 | Burch et al. | |
| 2004/0105899 A1 | 6/2004 | Dowdle et al. | |
| 2005/0009721 A1 | 1/2005 | Delplancke et al. | |
| 2005/0020805 A1 | 1/2005 | Sunkara et al. | |
| 2005/0069997 A1 | 3/2005 | Adkasson et al. | |
| 2005/0154114 A1 | 7/2005 | Hale | |
| 2006/0035808 A1 | 2/2006 | Ahmed et al. | |
| 2006/0110610 A1 | 5/2006 | Matsutan et al. | |
| 2006/0110810 A1 | 5/2006 | Raigarhia et al. | |
| 2006/0148053 A1 | 7/2006 | Emptage et al. | |
| 2007/0193960 A1 | 8/2007 | Frank et al. | |
| 2007/0202062 A1* | 8/2007 | Workman | A61Q 5/02 424/66 |
| 2007/0207113 A1 | 9/2007 | Joerger et al. | |

(Continued)

FOREIGN PATENT DOCUMENTS

| CN | 1687433 | 10/2005 |
|---|---|---|
| EP | 1604647 | 12/2005 |

(Continued)

OTHER PUBLICATIONS

Kunioka Masao, "Possible Incorporation of Petroleum-based Carbons in Biochemicals Produced by Bioprocess", Applied Microbiology, 2010, vol. 87, pp. 491-497.
Material Safety Data Sheet, "1,3-Propanediol", Anachemia Science, Canada, Nov. 22, 2011, pp. 1-4.
Material Safety Data Sheet, "1.3-Propanediol", Santa Cruz Biotechnology, Inc., Issue Date: Oct. 21, 2009, Print Date: Aug. 6, 2011— pp. 1-6.
Mark, Raymond, "H-27328: Modified Draize Repeater.1 Insult Patch Test Study in Human Volunteers", Trade Secret White Paper, Sponsored by E.I. DuPont De Nemours and Company, Jan. 30. 2006, pp. 1-32.
Beek, L. Van, "Primary Skin and Eye Irritation Tests with Propanediol-1,3 in Albino Rabbits", Central Institute for Nutrition and Food Research, pp. 1-7, 1973.

(Continued)

*Primary Examiner* — Aradhana Sasan
(74) *Attorney, Agent, or Firm* — McCarter & English, LLP

(57) ABSTRACT

The present disclosure relates to a deodorant containing 1,3-propanediol. In particular, the present disclosure relates to a clear, natural deodorant that is safe and effective, can minimize microbial activity, can contain sufficient amounts of fragrance to mask malodor, or both, in a formulation substantially free of petroleum derived components, antibacterial and/or antifungal agents, or both.

19 Claims, No Drawings

(56) References Cited

U.S. PATENT DOCUMENTS

| | | |
|---|---|---|
| 2007/0241306 A1 | 10/2007 | Wehner et al. |
| 2007/0275139 A1 | 11/2007 | Joerger et al. |
| 2008/0176957 A1* | 7/2008 | Joerger .................. A61K 8/06 514/738 |
| 2014/0255077 A1* | 9/2014 | Mobarak ................ A45D 40/00 401/88 |

FOREIGN PATENT DOCUMENTS

| | | |
|---|---|---|
| JP | 5221821 | 8/1993 |
| JP | H06234935 | 8/1994 |
| JP | 07090294 | 4/1995 |
| JP | 8183721 | 7/1996 |
| JP | 10081615 | 3/1998 |
| JP | 2002138069 | 5/2002 |
| JP | 200515401 | 1/2005 |
| WO | 2004101479 | 11/2004 |

OTHER PUBLICATIONS

Thwaites, Fredrik T., "Carbon 14: New Approach to the Glacial Age", The Wisconsin Magazine of History, Summer 1952, vol. 35, No. 4 pp. 277-279.

Chen, G.F., "Cyclization during Polyesterification: Isolation of an 18-Member Ring Compound from Reaction of Phthalic Anhydride with 2,2-Dimethyl-1,3-Propanediol", Journal of Applied Polymer Science, 1990, vol. 41, Issues 9-10, pp. 2517-2520.

Fung, Inez Y. , et al., "Evolution of Carbon Sinks in a Changing Climate", PNAS, Aug. 9, 2005, vol. 12, No. 32, pp. 11201-11206.

Jabrane, S., et al. "Study of the Thermal Behaviour of 1,3-Propanediol and its Aqueous Solutions", Thermochimica Acta 311 (1998); pp. 121-127.

"Industrial Bioproducts: Today and Tomorrow" (Paster, et al.) Prepared by Energetics, Inc., for the U.S. Department of Energy, Jul. 2003, See p. 1 and 2, Table 1-1 and 1-6.

Huang, He, et al., "Production of 1,3-Propanediol by Klebsiella Pneumoniae", Applied Biochemistry and Biotechnology, 2002, vol. 98-100, pp. 687-698.

Wittooff, Harold, et al., (Industrial Organic Chemicals 2004), Wiley-IEEE, p. 155-156.

Meldola. Raphael, "The Chemical Synthesis of Vital Products and the Interrelations Between Organic Compounds", 1904, pp. 95-96 in part, 2 pages.

Blomstrom, Dale C., et al. "Plants Metabolise Ethylene to Ethylene Glycol", Nature 1980, vol. 283, pp. 66-83—1 Page—Abstract.

Galinsky Raymond E., et al., "Basic Pharmacokinetics", Remington, The Science and Practice of Pharmacy, 21st Edition, Lippincott Williams & Wilkins, 2006, p. 1171.

Belcher, Leigh A., et al., "Evaluating 1,3-Propanediol for Potential Skin Effects", Cosmetic & Toiletries. May 2010, vol. 125, No. 5, pp. 81-86.

Merriam-Webster Online Dictionary (online), Merriam-Webster Online, 2008 (retrieved on Jul. 28, 2008), Retrieved from the Internet <URL:http://www.merriam-webster.com/dictionary/ore.

Pesticide Action Network, (PAN) Pesticides Database (online), www.pesticideinfo.org, 2008 (retrieved on Jul. 30, 2008). Retrieved from the Internet: <URL:http://www.pesticideinfo.org/Detail.sub---Chemical.JSP?Rec.sub--Id=PC342-62.

\* cited by examiner

DEODORANTS CONTAINING 1,3-PROPANEDIOL

CROSS-REFERENCE TO RELATED APPLICATIONS

This application claims priority to U.S. Provisional Application Ser. No. 62/201,261, filed Aug. 5, 2015, the entire contents of which are incorporated herein by reference.

FIELD OF THE TECHNOLOGY

The present disclosure relates to a deodorant containing 1,3-propanediol. In particular, the present disclosure relates to a stick or roll-on deodorant containing 1,3-propanediol that is safe and effective.

BACKGROUND

A deodorant is a substance applied to the body to prevent body odor caused by the bacterial breakdown of perspiration in armpits, feet, and other areas of the body. An antiperspirant, or antiperspirant deodorant, is a subset of deodorants that also prevent sweating by affecting sweat glands.

Deodorants and antiperspirants come in many forms, including sticks, gels, creams, roll-ons and aerosol sprays. These different forms can be clear, translucent or opaque. Clear deodorants and antiperspirants are preferred because they are thought to leave less visible residue, but often clear deodorants and antiperspirants suffer from performance issues such as stability or stickiness.

The application of deodorants and antiperspirants to the body is also important. The deodorant and antiperspirant should dry quickly and provide a soft, smooth feel. Some quick drying deodorants and antiperspirants can also suffer performance issues, such as the roll-on applicator can dry out or the applicator ball can stop rolling. In some antiperspirants, after application to the skin the antiperspirant salt can precipitate out of solution onto the skin surface.

The present disclosure relates to different deodorant compositions containing) 1,3-propanediol that can be clear, natural, stable and/or fast drying, and that are safe and effective.

SUMMARY

The present disclosure relates to a deodorant containing 1,3-propanediol. In particular, the present disclosure relates to stick and roll-on deodorants containing 1,3-propanediol that are safe and effective.

In one embodiment, the present disclosure relates to a clear deodorant including 1,3-propanediol, solubilizer and fragrance. The solubilizer can contain polyglyceryl, polyglycerin or combinations thereof. For example, in another embodiment, the present disclosure relates to a deodorant including 1,3-propanediol, polyglyceryl, surfactant and fragrance.

The deodorant can be a natural deodorant and can be substantially free of petroleum derived components. It can also be substantially free of antibacterial agents, antifungal agents, or both. The deodorant can be a clear, antiperspirant deodorant further including an antiperspirant salt. The deodorant can be either a stick deodorant or a roll-on antiperspirant deodorant.

In another embodiment, the present disclosure relates to an antiperspirant deodorant including 1,3-propanediol, an emulsifier, a volatile silicone and an antiperspirant salt. The antiperspirant deodorant can be substantially free of polar emollients.

In another embodiment, the present disclosure relates to a method of making a clear, natural stick deodorant, including providing an aqueous solution of 1,3-propanediol, wherein the solution contains at least about 50% 1,3-propanediol and the pH of the solution is above 7, heating the solution to between about 80-100° C., mixing a fatty acid into the solution, mixing a solubilizer into the solution, cooling the solution to about 80° C. or below, and mixing fragrance into the solution to make the deodorant. The final clear solution can be safely and effectively transferred to packaging while the clear solution is heated, e.g., about 80° C.

In another embodiment, the present disclosure relates to a method of making an antiperspirant deodorant, including mixing volatile silicone and emulsifier together to form an oil phase, heating the oil phase to above about 50° C., mixing 1,3-propanediol and water together for form an aqueous phase, heating the aqueous phase to above about 50° C., mixing the oil phase and the aqueous phase together form a solution, cooling the solution to form an emulsion solution, mixing antiperspirant salt into the emulsion solution, and mixing fragrance into the emulsion solution to make the antiperspirant deodorant.

In another embodiment, the present disclosure relates to a method of making a clear antiperspirant deodorant, including mixing 1,3-propanediol and solubilizer together to form a solution, mixing fragrance into the solution, mixing water into the solution, mixing antiperspirant salt into the solution to make the antiperspirant deodorant.

DETAILED DESCRIPTION

The present disclosure relates to a deodorant containing 1,3-propanediol. In particular, the present disclosure relates to stick and roll-on deodorants containing 1,3-propanediol that are safe and effective.

The term "deodorant" as used herein is intended to include deodorants, as well as antiperspirants and antiperspirant deodorants. Deodorants such as stick deodorants, are typically made using a combination of propylene glycol (PG), soap, water, fragrance and an antibacterial and/or antifungal agent (e.g., triclosan). Fragrance are used to mask malodor caused by microbial activity. PG, or a similar compound, is needed to help solubilize the fragrance. An antibacterial and/or antifungal agent is used to reduce microbial activity that causes malodor. Some deodorants also contain aluminum salts, or similar components as antiperspirants, which also indirectly help to reduce microbial activity by reducing the water present.

The use of petroleum derived components, e.g., PG, in deodorant can cause irritation and/or sensitivity. The use of antibacterial and/or antifungal agents, e.g., triclosan, has the potential to cause the proliferation of antibiotic-resistant bacteria, act as endocrine disruptors, impair the development of a proper immune system, and damage the environment. Without PG or triclosan, however, a deodorant cannot minimize microbial activity or contain sufficient amounts of fragrance to mask the malodor.

In one embodiment, the present disclosure relates to a clear, natural deodorant that is safe and effective, can minimize microbial activity, can contain sufficient amounts of fragrance to mask malodor, or both, in a formulation substantially free of petroleum derived components, antibacterial and/or antifungal agents, or both.

In one embodiment, the present disclosure relates to a clear deodorant including 1,3-propanediol, solubilizer and fragrance, wherein the deodorant is clear.

The deodorant can contain about, more than about, or less than about 30, 40, 50, 60, 70, 80 or about 90 wt % 1,3-propanediol. These values can be used to define a range such as about 30 to about 90 wt %, about 40 to about 80 wt %, about 50 to about 70 wt %, in one embodiment, the deodorant contains about 60 wt % of 1,3-propanediol.

The 1,3-propanediol can be biologically derived, such as by fermentation (e.g., Zemea® Propanediol by DuPont fate & Lyle). The 1,3-propanediol can be derived from microorganism metabolism of plant-derived sugars composed of carbon of atmospheric origin, and not composed of fossil-fuel carbon. The deodorant can be biodegradable in which the biologically derived 1,3-propanediol and/or other components can have an anthropogenic $CO_2$ emission profile of zero (0). The term "biodegradable" means the capacity of a composition or compound to be broken down by living organisms to simple, stable compounds such as carbon dioxide and water in a relatively short time, e.g., less than years or months, as opposed to plastics. An "anthropogenic emission profile" means anthropogenic $CO_2$ emissions that are contributed to the atmosphere upon biodegradation of a compound or composition.

Whereas photosynthesis is the process of creating growing matter through the conversion of carbon dioxide ($CO_2$) and water ($H_2O$) into plant material through the action of the sun, biodegradation is the process of converting organic material back into $CO_2$ and $H_2O$ through the activity of living organisms. There are many published test methods for measuring the biodegradability of organic chemicals such as glycols. One internationally recognized method is ASTM E1720-01, Standard Test Method for Determining Ready, Ultimate Biodegradability of Organic Chemicals in a Sealed Vessel $CO_2$ Production Test.

"Carbon of atmospheric origin" as used herein refers to carbon atoms from carbon dioxide molecules that have recently, in the last few decades, been free in the earth's atmosphere Such carbons in mass are identifiable by the present of particular radioisotopes as described herein. "Green carbon", "atmospheric carbon", "environmentally friendly carbon", "life-cycle carbon", "non-fossil fuel based carbon", "non-petroleum based carbon", "carbon of atmospheric origin", and "biobased carbon" are used synonymously herein.

"Carbon of fossil origin" as used herein refers to carbon of petrochemical origin. Such carbon has not been exposed to UV rays as atmospheric carbon has, therefore masses of carbon of fossil origin has few radioisotopes in their population. Carbon of fossil origin is identifiable by means described herein. "Fossil fuel carbon", "fossil carbon", "polluting carbon", "petrochemical carbon", "petro-carbon" and carbon of fossil origin are used synonymously herein.

"Renewably-based" denotes that the carbon content of the 1,3-propanediol is from a "new carbon" source as measured by ASTM test method D 6866-05 Determining the Biobased Content of Natural Range Materials Using Radiocarbon and Isotope Ratio Mass Spectrometry Analysis, incorporated herein by reference. This test method measures the C-14/C-12 isotope ratio in a sample and compares it to the C-14/C-12 isotope ratio in a standard 100% biobased material to give percent biobased content of the sample, "Biobased materials" are organic materials in which the carbon comes from recently (on a human time scale) fixated $CO_2$ present in the atmosphere using sunlight energy (photosynthesis). On land, this $CO_2$ is captured or fixated by plant life (e.g., agricultural crops or forestry materials). In the oceans, the $CO_2$ is captured or fixated by photosynthesizing bacteria or phytoplankton. A biobased material has a C-14/C-12 isotope ratio in range of from 1:0 to greater than 0:1. Contrarily, a fossil-based material, has a C-14/C-12 isotope ratio of 0:1.

A small amount of the carbon dioxide in the atmosphere is radioactive. This C-14 carbon dioxide is created when nitrogen is struck by an ultra-violet light produced neutron, causing the nitrogen to lose a proton and form carbon of molecular weight 14 which is immediately oxidized in carbon dioxide. This radioactive isotope represents a small but measurable fraction of atmospheric carbon. Atmospheric carbon dioxide is cycled by green plants to make organic molecules during the process known as photosynthesis. The cycle is completed when the green plants or other forms of life metabolize the organic molecules producing carbon dioxide which is released back to the atmosphere. Virtually all forms of life on Earth depend on this green plant production of organic molecule to produce the chemical energy that facilitates growth and reproduction. Therefore, the C-14 that exists in the atmosphere becomes part of all life forms, and their biological products. These renewably based organic molecules that biodegrade to $CO_2$ do not contribute to global warming as there is no net increase of carbon emitted to the atmosphere. In contrast, fossil fuel based carbon does not have the signature radiocarbon ratio of atmospheric carbon dioxide.

The biologically derived 1,3-propanediol can be substantially purified. "Substantially purified" means the biologically-produced 1,3-propanediol has one or more of the following characteristics: (1) an ultraviolet absorption at 220 nm of less than about 0.200 and at 250 nm of less than about 0.075 and at 275 nm of less than about 0.075; or (2) a composition having L*a*b* "b*" color value of less than about 0.15 and an absorbance at 270 nm of less than about 0.075; or (3) a peroxide composition of less than about 200, 150, 100, 50, 40, 30, 20, 10, 5, 1 or about 0.5 ppm; or (4) a concentration of total organic impurities of less than about 1,000, 900, 800, 700, 600, 500, 400, 300, 200, 150, 100, 50 or about 10 ppm. Any of these sets of values can be used to define a range, such as a peroxide composition of about 100 to about 1 ppm.

A "b*" value is the spectrophotometrically determined "Yellow Blue measurement as defined by the CIE L*a*b* measurement ASTM D6290.

By the terms "color" and "color bodies" is meant the existence of visible color that can be quantified using a spectrocolorimeter in the range of visible light, using wavelengths of approximately 400-800 nm, and by comparison with pure water. Reaction conditions can have an important effect on the nature of color production. Examples of relevant conditions include the temperatures used, the catalyst and amount of catalyst. While not wishing to be bound by theory, we believe color precursors include trace amounts of impurities comprising olefinic bonds, acetals and other carbonyl compounds, peroxides, etc. At least some of these impurities may be detected by such methods as UV spectroscopy, or peroxide titration.

The peroxide composition in ppm and total organic impurities can be determined by standard analytical techniques, including gas chromatography.

It is believed that the aforementioned purity level parameters for biologically-derived and purified 1,3-propanediol distinguishes such compositions from 1,3-propanediol compositions prepared from chemically purified 1,3-propanediol derived from petroleum sources and/or from biologically purified 1,3-propanediol not exhibiting such purity values.

The deodorants of the present disclosure can include 1,3-propanediol and/or other components having at least 1, 2, 3, 4, 5, 10, 20, 30, 40, 50, 60, 70, 80, 90, 95, 99, 100% biobased carbon.

The deodorant can contain about, more than about, or less than about 4, 5, 6, 7, 8, 9, 10, 11 or about 12 wt % solubilizer. These values can be used to define a range such as about 4 to about 12 wt %, about 6 to about 10 wt %, about 7 to about 9 wt %. In one embodiment, the deodorant contains about 8 wt % of solubilizer. The solubilizer can contain polyglyceryl, polyglycerin or combinations thereof. For example, the ratio of polyglyceryl to polyglycerin can be about 100:0, 99:1, 98:2, 97:3, 96:4, 95:5, 94:6, 93:7, 92:8, 91:9, 9:1, 89:11, 88:12, 87:13, 86:14, 85:15, 84:16, 83:17, 82:18, 81:19 or about 8:2. These values can be used to define a range such as about 98:2 to about 96:4. In one embodiment, the solubilizer contains about 97 wt % polyglyceryl and about 3 wt % polyglycerin.

The solubilizer can contain a non-ethoxylated nonionic surfactant, such as alkyl polyglucosides, alkyl polypentosides, polyglyceryl esters, polyglyceryl ethers, polyglyceryl sorbitan fatty acid esters, sucrose esters, and sorbitan esters, and combinations thereof. Examples of non-ethoxylated nonionic surfactants include C8-C18 polyglyceryl monoesters (e.g., polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and combinations thereof) and C8-C18 polyglyceryl monoethers (e.g., polyglyceryl-4 lauryl ether, polyglyceryl-10 lauryl ether.) In one embodiment, the solubilizer includes polyglyceryl-10 caprylate/caprate, which can be obtained from Lonza as POLYALDO®10-1-CC KFG (Lonza).

The deodorant can contain about, more than about, or less than about 0.1, 0.2, 0.3, 0.4, 0.5, 0.6, 0.7, 0.8, 0.9, 1, 1.5, 2, 2.5, 3, 3.5, 4, 4.5 or about 5 wt % fragrance. These values can be used to define a range such as about 0.2 to about 3 wt %, about 0.25 to about 2 wt %, about 0.4 to about 1 wt %. In one embodiment, the deodorant contains about 0.5 wt % of a fragrance. The fragrance can be any known fragrance used in the deodorant field.

The deodorant can be clear (transparent), including a solid clear composition. The clear deodorant and/or antiperspirant compositions of the present disclosure can be sticks, gels, creams or roll-on. The term "clear" or "transparent" refers to their usual dictionary definition; thus, for example, a clear, stick composition can allow viewing of objects behind it. By contrast, a translucent composition, although allowing light to pass through, causes the light to be scattered so that it will be difficult or impossible to see clearly objects behind the translucent composition. An opaque composition does not allow light, or significant amount of light, to pass therethrough. Within the context of the present disclosure, a stick is clear or transparent if the maximum transmittance of light of any wavelength in the range 400-800 nm through a sample 1 cm thick is at least 20%, 25%, 30%, 35%, 40%, 45%, and in particular at least 50%. The transmittance can be measured by placing a sample of the aforementioned thickness into a light beam of a spectrophotometer whose working range includes the visible spectrum.

The deodorant can also contain a surfactant. The deodorant can contain about, more than about, or less than about 2, 3, 4, 5, 6, 7, 8, 9, 10, 11, 12, 13, 14 or about 15 wt % surfactant. These values can be used to define a range such as about 2 to about 15 wt %, about 4 to about 8 wt %, about 5 to about 7 wt %. In one embodiment, the deodorant contains about 6 wt % of a surfactant. The surfactant can be formed from the reaction of a fatty acid with a base, e.g., a 10% solution of NaOH. The fatty acid can be any fatty acid capable of forming a surfactant for use in deodorants, such as lauric acid, linoleic acid, linolenic acid, oleic acid, palmitic acid, ricinoleic acid, stearic acid, myristic acid or combinations thereof. The base can be any base, such as NaOH. The deodorant can contain fatty acid, base and/or trace amount of both. The deodorant can also contain water.

The deodorant or antiperspirant of the present disclosure can also be natural deodorant or antiperspirant and can be substantially free of petroleum derived components, such as less than about 10 wt %, 9, 8, 7, 6, 5, 4, 3, 2, 1, 0.5 or 0.1 wt % petroleum derived components.

The deodorant or antiperspirant of the present disclosure can be substantially free of antibacterial agents, antifungal agents, or both, such as less than about 10 wt %, 9, 8, 7, 6, 5, 4, 3, 2, 1, 0.5 or 0.1 wt % antibacterial agents, antifungal agents, or both.

In a particular embodiment, the deodorant can be a stick deodorant and can include 1,3-propanediol, particularly about 50 to about 70 wt %; polyglyceryl, particularly about 7 to about 9 wt %, surfactant, particularly about 5 to about 7 wt %, fragrance, particularly about 0.25 to about 1.5 wt % and water. Table 1 below lists additional embodiments of the present disclosure.

TABLE 1

Additional Deodorant Embodiments

| Component 1 | Name | Wt % |
|---|---|---|
| 1,3-Propanediol | Zemea ® Propanediol | 50-70% |
| Solubilizer | POLYALDO ® 10-1-CCKFG | 7-9% |
| Fatty Acid | Stearic Acid | 4-8% |
| Basic Solution | 10% NaOH solution | 8-12% |
| Fragrance | Fragrance | 0.25-1.5% |
| Water | Water | 10-20% |

In one embodiment, a clear deodorant or antiperspirant can be formed when all the components are soluble in each other and form a single phase product. For example, fragrance is difficult to solubilize in a typical deodorant. The relatively high amount of 1,3-propanediol present in the stick deodorant of the present disclosure can aid in solubilizing fragrances. The relatively high amount of 1,3-propanediol can provide a firm, clear deodorant stick. The solubilizer present in the deodorant of the present disclosure can also aid in solubilizing fragrances. The solubilizer can provide a clear deodorant stick that does not cause stickiness.

In one embodiment, the clear, natural stick deodorant of the present disclosure exhibits good application properties, such as rigidity, hardness, feel, stickiness, tackiness or combinations thereof.

In another embodiment, the present disclosure relates to a method of making a deodorant, including providing an aqueous solution of 1,3-propanediol, wherein the solution contains at least about 50% 1,3-propanediol and the pH of the solution is above 7, heating the solution to between about 80-100° C., mixing a fatty acid into the solution, mixing a solubilizer into the solution, cooling the solution to about 80° C. or below, and mixing fragrance into the solution make the deodorant. At one or more of the steps, the solution can be stirred to obtain and maintain a clear solution.

The aqueous solution of 1,3-propanediol can contain about, more than about, or less than about 10, 20, 30, 40, 50, 60, 70, or 80 wt % 1,3-propanediol. These values can also be used to define a range, such as about 60 to about 80 wt %. The pH of the aqueous solution can be greater than about 7, 7.5, 8, 8.5, 9, 9.5, 10, 11 or about 12. These values can also be used to define a range, such as about 8 to about 10.

Because the method includes heating, the water present can evaporate. The amount of water evaporated out of the solution can be added back to the solution at one or more different times. For example, before, after or concurrent with the cooling step, water can be added to the solution in the approximate amount that evaporated during the prior steps.

Once the deodorant formulation is combined and mixed, the method can include transferring the deodorant to packaging while the temperature of the clear solution is between 25-80° C.

Deodorants and antiperspirants function to reduce odor, reduce sweat, deliver fragrance, or combinations thereof. To do so most effectively, the deodorant should have a stable formulation. Deodorants, e.g., roll-on antiperspirant deodorants, are typically made using either polar emollients or other emulsifiers that can cause poor performance, such as the roll-on applicator drying out, the applicator ball becoming stuck or stickiness of the applied deodorant.

The present disclosure also relates to a roll-on antiperspirant deodorant that can have a relatively fast drying time, keep the roll-on applicator from drying out or the ball from becoming stuck and can effectively deliver antiperspirant salts and/or fragrance, or combinations thereof.

In one embodiment, the present disclosure relates to an antiperspirant deodorant including 1,3-propanediol, emulsifier, a volatile silicone, and an antiperspirant salt. The antiperspirant deodorant can be a roll-on antiperspirant deodorant.

The antiperspirant deodorant can contain about, more than about, or less than about 1, 2, 3, 4, 5, 6, 7, 8, 9, 10, 11, 12, 13, 14, 15, 16, 17, 18, 19, 20, 21, 22, 23, 24, 25, 26, 27, 28, 29 or about 30 wt % 1,3-propanediol. These values can be used to define a range such as about 3 to about 15 wt %, about 5 to about 9 wt %. In one embodiment, the antiperspirant deodorant contains about 7 wt % 1,3-propanediol. The 1,3-propanediol can be biologically derived, such as by fermentation (e.g., Zemea® Propanediol by DuPont Tate & Lyle).

The antiperspirant deodorant can contain about, more than about, or less than about 1, 2, 3, 4, 5, 6, 7, 8, 9, 10, 11, 12, 13, 14, 15, 16, 17, 18, 19 or about 20 wt % emulsifier. These values can be used to define a range such as about 1 to about 10 wt %, about 2 to about 8 wt %, about 3 to about 6 wt %. In one embodiment, the antiperspirant deodorant contains about 4 wt % emulsifier. The emulsifier can contain one or more polyoxyl stearyl ethers, such as PEG-2 stearyl ether (Steareth-2), PEG-21 stearyl ether Steareth-21), or combinations thereof. In one embodiment, the emulsifier contains about 2 wt % PEG-2 stearyl ether and about 2 wt % PEG-21 stearyl ether.

The antiperspirant deodorant can contain about, more than about, or less than about 1, 2, 3, 4, 5, 6, 7, 8.9, 10, 11, 12, 13, 14, 15, 16, 17, 18, 19 or about 20 wt % of volatile silicone. These values can be used to define a range such as about 1 to about 10 wt %, about 3 to about 7 wt %. In one embodiment, the antiperspirant deodorant contains about 5 wt % of volatile silicone. The volatile silicone can be cyclomethicone, such as hexamethylcyclotrisiloxane, octamethylcyclotetrasiloxane, decamethylcyclopentasiloxane, dodecamethylcyclohexasiloxane, or combination thereof.

The antiperspirant deodorant can contain about, more than about, or less than about 5, 6, 7, 8, 9, 10, 11, 12, 13, 14, 15, 16, 17, 18, 19, 20, 21, 22, 23, 24, 25, 26, 27, 28, 29 or about 30 wt % of antiperspirant salt or complex. These values can be used to define a range such as about 5 to about 25 wt %, about 10 to about 20 wt %. In one embodiment, the antiperspirant deodorant contains about 15 wt % of antiperspirant salt or complex. The antiperspirant salt or complex can be any metal salt, or any aluminum-based complex, known to prevent or reduce sweating, including aluminium chloride, aluminum chlorohydrate-dehydrate, aluminium chlorohydrate, and aluminium-zirconium (e.g., aluminium zirconium tetrachlorohydrex gly, aluminium zirconium trichlorohydrex gly). The antiperspirant salt or complex can also be a natural deodorant crystal, such as an alum salty such as potassium alum or ammonium alum.

The deodorant or antiperspirant of the present disclosure can be substantially free of polar emollients, such as less than about 10 wt %, 9, 8, 7, 6, 5, 4, 3, 2, 1, 0.5 or 0.1 wt % polar emollients.

In another embodiment, the present disclosure relates to a method of making an antiperspirant deodorant, including mixing volatile silicone and emulsifier together to form an oil phase, heating the oil phase to above about 50° C., mixing 1,3-propanediol and water together for form an aqueous phase, heating the aqueous phase to above about 50° C., mixing the oil phase and the aqueous phase together form a solution, cooling the solution to form an emulsion solution, mixing antiperspirant salt into the emulsion solution, and mixing fragrance into the emulsion solution to make the antiperspirant deodorant.

The oil phase and the aqueous phase can each be heated to about or above about 50° C., 55° C., 60° C., 65° C., 70° C. or about 75° C. In some embodiments, the aqueous phase is heated and held at an equal or a slightly higher temperature, e.g., about 1° C., 2° C., 3° C., 4° C., or about 5° C., than the oil phase when mixed together to improve the emulsion formation.

In yet another embodiment, the present disclosure relates to a clear, antiperspirant deodorant including 1,3-propanediol, solubilizer, fragrance, and antiperspirant salt, wherein the deodorant is clear. The clear, antiperspirant deodorant can be a roll-on.

The antiperspirant deodorant can contain about, more than about, or less than about 1, 2, 3, 4, 5, 6, 7, 8, 9, 10, 11, 12, 13, 14, 15, 16, 17, 18, 19 or about 20 wt % 1,3-propanediol. These values can be used to define a range such as about 5 to about 15 wt %, about 7 to about 13 wt %, about 8 to about 12 wt %. In one embodiment, the antiperspirant deodorant contains about 10 wt % 1,3-propanediol. The 1,3-propanediol can be biologically derived, such as by fermentation (e.g., Zemea® Propanediol by DuPont Tate & Lyle).

The antiperspirant deodorant can contain about, more than about, or less than about 2, 3, 4, 5, 6, 7, 8, 9, 10, 11, 12, 13, 14, 15, 16, 17, 18, 19 or about 20 wt % solubilizer. These values can be used to define a range such as about 1 to about 10 wt %, about 2 to about 9 wt %, about 4 to about 6 wt %, In one embodiment, the deodorant contains about 5 wt % of solubilizer. The solubilizer can contain polyglyceryl, polyglycerin or combinations thereof. For example, the ratio of polyglyceryl to polyglycerin can be about 100:0, 99:1, 98:2, 97:3, 96:4, 95:5, 94:6, 93:7, 92:8, 91:9, 9:1, 89:11, 88:12, 87:13, 86:14, 85:1.5, 84:16, 83:17, 82:18, 81:19 or about 8:2. These values can be used to define a range such as about 98:2 to about 96:4. In one embodiment, the solubilizer contains about 97 wt % polyglyceryl and about 3 wt % polyglycerin.

The solubilizer can contain a non-ethoxylated nonionic surfactant, such as alkyl polyglucosides, alkyl polypentosides, polyglyceryl esters, polyglyceryl ethers, polyglyceryl sorbitan fatty acid esters, sucrose esters, and sorbitan esters, and combinations thereof. Examples of non-ethoxylated nonionic surfactants include C8-C18 polyglyceryl monoesters (e.g., polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and combinations thereof) and C8-C18 polyglyceryl monoethers (e.g., polyglyceryl-4 lauryl ether, polyglyceryl-10 lauryl ether.) In one embodiment, the solubilizer includes polyglyceryl-10 caprylate/caprate, which can be obtained from Lonza as POLYALDO® 10-1-CC KFG (Lonza).

The clear, antiperspirant deodorant can also be natural wherein the antiperspirant salt is a natural antiperspirant salt. The antiperspirant deodorant can substantially free of petroleum derived components, antibacterial agents, antifungal agents, or both, or combinations thereof.

In other embodiments of the present disclosure, the deodorant and antiperspirant can contain petroleum derived components, antibacterial agents, antifungal agents, or both, or combinations thereof.

In another embodiment, the present disclosure relates to a method of making a clear antiperspirant deodorant, including mixing 1,3-propanediol and solubilizer together to form a solution, mixing fragrance into the solution, mixing water into the solution, mixing antiperspirant salt into the solution to make the antiperspirant deodorant. The water can be mixed into the solution slowly with agitation.

The disclosures of all cited references including publications, patents, and patent applications are expressly incorporated herein by reference in their entirety.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention is further defined in the following Examples. It should be understood that these Examples, while indicating preferred embodiments of the invention, are given by way of illustration only.

EXAMPLES

Example 1

A clear, natural deodorant was prepared. The ingredients and the amount of each ingredient in the final deodorant composition is provided in Table 2. The deodorant does not contain petroleum derived components or bacteriostats.

TABLE 2

Clear, Natural Deodorant Stick

| Phase | Ingredients | Wt % |
|---|---|---|
| A | Distilled Water | 16% |
| | Zemea ® Propanediol | 60% |
| | Sodium Hydroxide (10% Sol.) | 9.5% |
| B | Stearic Acid | 6% |
| C | POLYALDO ® 10-1-CCKFG | 8% |
| D | Fragrance | 0.5% |

A basic solution of 1,3-propanediol (Zemea® Propanediol) was prepared (Phase A). The basic solution was heated to about 90° C. while being stirred. The basic solution was kept below 100° C. to avoid boiling. Stearic acid flakes (Phase B) were then added to the basic solution while it was held at about 90° C. The stearic acid was added while the basic solution was stirred. The basic solution was stirred until the stearic acid dissolved and the solution became clear.

After the solution became clear, the clear solution was removed from the heat source and the solubilizer was added (Phase C). The solubilizer was added while the clear solution was stirred. The solution was stirred until the solution became clear again. The clear solution was heated to about 80° C. and the fragrance was then added to the solution (Phase D). The solution was stirred while the fragrance was added and until the solution became clear again.

The solution was again removed from heat and allowed to cool to below 80° C. While cooling, the solution was transferred to the deodorant stick packaging and allowed to cool. The cooled and final deodorant composition did not exhibit any shrinkage in the packaging after being transferred in a heated state.

Typically, a deodorant composition is prepared by mixing the polyol and solubilizer together. Here, the polyol is added first with other components, the soap is formed and then the solubilizer is added just prior to the fragrance. The order of the present method was found to provide and maintain a clear deodorant exhibiting superior properties. The deodorant stick was tested for firmness and was found to be as firm or firmer than other leading commercial deodorant sticks, surprising in light of the relatively high amount of 1,3-propanediol present.

Also, a typical deodorant composition containing over 50% of a polyol, such as glycerin or PG, results in a sticky deodorant. Surprisingly, the deodorant has 60% 1,3-propanediol and does not exhibit stickiness. Similarly, a deodorant composition containing a high amount of solubilizer also results in a sticky deodorant. Here, the deodorant contains high levels of solubilizer but does not exhibit stickiness.

The deodorant also functions to reduce malodor. Without wishing to be bound, it is believed that the high level of 1,3-propanediol displaces and reduces water activity. The reduced water activity reducing microbial growth and the resulting malodor.

Example 2

A roll-on antiperspirant deodorant was prepared. The ingredients and the amount of each ingredient in the final antiperspirant deodorant composition is provided in Table 3.

TABLE 3

Antiperspirant Deodorant Roll-on

| Phase | Ingredients | Wt % |
|---|---|---|
| A | Cyclomethicone | 5% |
|   | Steareth-2 | 2% |
|   | Steareth-21 | 2% |
| B | Zemea ® Propanediol | 7% |
|   | Silica | 0.2% |
|   | Distilled Water | 68.8% |
| C | Aluminum Chlorohydrate, Dihydrate | 15% |

The volatile silicone (cyclomethicone) and the emulsifier(s) (Steareth-2 and -21) were mixed together (Phase A). The mixture was heated to about 70° C. while being stirred until the wax was completed melted. The emulsifiers were sampled from drums. The emulsifiers were solid at room temperature. The drums were heated and shaken to ensure a representative sample was used.

The 1,3-propanediol (Zemea® Propanediol) silica and distilled water were mixed together (Phase B). The mixture was heated to about 72° C. while being stirred. Phase A was added to Phase B with stirring to form a solution. The solution was stirred until homogeneous and the desired particle size was obtained. The solution was removed from the heat with continued stirring. The emulsion was allowed to form.

Once the emulsion was formed, the antiperspirant salt, aluminum chlorohydrate, dehydrate, was mixed into the emulsion solution. The salt was added slowly and mixed until fully dissolved. The emulsion solution was then cooled. The fragrance was mixed into the emulsion solution to form the antiperspirant deodorant. After the antiperspirant deodorant cooled to about room temperature, the antiperspirant deodorant was transferred to a roll-on container. A low viscosity emulsion antiperspirant roll-on is obtained with a smooth texture. It has a short drying time and non-greasy feeling.

It was discovered that 1,3-propanediol, and aqueous solution of 1,3-propanediol, have the ability to dissolve high levels of antiperspirant salts. 1,3-propanediol can act as a second solvent for the antiperspirant salt in a roll-on formulation, such that if the aqueous solution evaporates the 1,3-propanediol remains and keeps the antiperspirant salts in solution. The 1,3-propanediol also prevents the roll-on ball from drying out and sticking.

In addition, antiperspirant deodorants traditionally do not contain volatile silicones. After application to the skin, volatile silicones and water evaporate rapidly from the skin's surface. The combination of volatile silicones and polar emollients in traditional antiperspirant deodorants can cause the antiperspirant salts to precipitate out of solution. The use of 1,3-propanediol allowed for the removal of polar emollients from the formulation, and the inclusion of volatile silicones.

The combination of volatile silicones and 1,3-propanediol did not encounter any application problems. The antiperspirant salts did not precipitate out of solution, but rather were applied and provided a soft, smooth and non-sticky feel. In addition, the use of a volatile silicone allows for relative faster drying time after application.

Example 3

An clear roll-on antiperspirant deodorant was prepared. The ingredients and the amount of each ingredient in the final clear antiperspirant deodorant composition is provided in Table 4.

TABLE 4

Clear Antiperspirant Deodorant Roll-on

| Phase | Ingredients | Wt, % |
|---|---|---|
| A | POLYALDO ® 10-1-CCKFG | 5% |
|   | Zemea ® Propanediol | 10% |
| B | Fragrance | 0.5% |
| C | Distilled Water | 69.5% |
| D | Aluminum Chlorohydrate, Dihydrate | 15% |

A solution of 1,3-propanediol (Zemea® Propanediol) and solublizer (POLYALDO®10-1-CCKFG) was prepared (Phase A). The solution was stirred. The combination of 1,3-propanediol and solubilizer did not exhibit any gelling, or any local gelling, of the solubilizer upon addition to the 1,3-propanediol.

The fragrance was mixed into the solution with stirring. Thereafter, the distilled water was slowly added to the solution with stirring until homogeneous. The mixture was clear at room temperature. The antiperspirant salts were mixed into the solution and stirred until fully dissolved. A low viscosity antiperspirant roll-on having a clear solution was formed.

The clear antiperspirant deodorant is easy to apply, stable (avoids drying out and keeps roller ball lubricated), PEG-free, and provides a smooth feel after application.

While this disclosure has been particularly shown and described with reference to example embodiments thereof, it will be understood by those skilled in the art that various changes in form and details may be made therein without departing from the scope of the invention encompassed by the appended claims.

We claim:

1. A deodorant consisting essentially of:
   (i) at least about 60% 1,3-propanediol by weight;
   (ii) at least about 8% polyglyceryl ester by weight; and
   (iii) a fragrance;
wherein the deodorant is clear, has a smooth texture, and is free of antibacterial agents and antifungal agents.

2. The deodorant of claim 1 wherein the deodorant is a natural deodorant and is substantially free of petroleum derived components.

3. The deodorant of claim 1 wherein the polyglyceryl ester comprises Polyaldo® 10-1-CC Polyglyceryl Ester.

4. The deodorant of claim 1 wherein the deodorant contains more than about 70 wt % 1,3-propanediol.

5. The deodorant of claim 1 wherein the deodorant is a stick deodorant.

6. The deodorant of claim 1 wherein the deodorant is a clear, antiperspirant deodorant further comprising an antiperspirant salt.

7. The deodorant of claim 4 wherein the antiperspirant deodorant is a roll-on deodorant.

8. The deodorant of claim 1 wherein the 1,3-propanediol has at least 1% biobased carbon.

9. The deodorant of claim 1 wherein the 1,3-propanediol is biologically-derived through a fermentation process.

10. The deodorant of claim 1 wherein the 1,3-propanediol has an ultraviolet absorption at 220 nm of less than about 0.200 and at 250 nm of less than about 0.075 and at 275 nm of less than about 0.075.

11. The deodorant of claim 1 wherein the 1,3-propanediol has a peroxide concentration of less than about 20 ppm.

12. The biodegradable composition of claim 1 wherein said 1,3-propanediol has a concentration of total organic impurities in said composition of less than about 800 ppm.

13. The deodorant of claim 1 further comprising about 2% to about 15% surfactant.

14. The deodorant of claim 13 wherein the surfactant comprises a stearate.

15. The deodorant of claim 14 wherein the stearate is formed from the reaction of stearic acid and sodium hydroxide.

16. The deodorant of claim 1 further comprising water.

17. The deodorant of claim 6, wherein the antiperspirant salt comprises at least one of aluminium chloride, aluminum chlorohydrate-dehydrate, aluminium chlorohydrate, and aluminium-zirconium.

18. The deodorant of claim 6, wherein the antiperspirant salt comprises a natural deodorant crystal, wherein the natural deodorant crystal comprises at least one of potassium alum and ammonium alum.

19. A deodorant comprising:
   (i) at least about 60% 1,3-propanediol by weight;
   (ii) at least about 8% polyglyceryl ester by weight; and
   (iii) a fragrance;
wherein the deodorant is clear, has a smooth texture, is a natural deodorant, is substantially free of petroleum derived components, and is free of antibacterial agents and antifungal agents.

* * * * *